United States Patent [19]
Zupancic et al.

[11] Patent Number: 4,969,167
[45] Date of Patent: Nov. 6, 1990

[54] CT SCANNER COOLING DUCT

[75] Inventors: Anton Z. Zupancic, Kirtland; Joseph S. Deucher, Lyndhurst, both of Ohio

[73] Assignee: Picker International, Inc., Highland Hts., Ohio

[21] Appl. No.: 385,019

[22] Filed: Jul. 25, 1989

Related U.S. Application Data

[63] Continuation of Ser. No. 276,070, Nov. 25, 1988, abandoned.

[51] Int. Cl.$^5$ .............................................. H05G 1/60
[52] U.S. Cl. ........................................ 378/19; 378/10; 378/199
[58] Field of Search ........................ 378/4, 19, 10, 199, 378/200

[56] References Cited

U.S. PATENT DOCUMENTS

| | | | |
|---|---|---|---|
| 4,456,826 | 6/1984 | Forster | 378/19 |
| 4,651,338 | 3/1987 | Hahn | 378/199 |
| 4,754,468 | 6/1988 | Mori | 378/19 |
| 4,831,639 | 5/1989 | Harke | 378/4 |

*Primary Examiner*—Craig E. Church
*Attorney, Agent, or Firm*—Fay, Sharpe, Beall, Fagan, Minnich & McKee

[57] ABSTRACT

A peripheral cooling duct (36) is mounted on a removable front door panel (26) of a CT scanner (10). A pressure source (74) supplies ambient air at elevated pressure through air inlet means (70) defined by an inner wall (78) of the cooling duct. Concentric flanges (58, 60) extending inward toward the inner region (76) of the CT scanner define a slit-like circular nozzle opening (56). Air is directed from the cooling duct through the nozzle opening across radiation detectors (20) for cooling the detectors and other features of the CT scanner during scanner operation.

20 Claims, 4 Drawing Sheets

CT SCANNER COOLING DUCT

This is a continuation of application Ser. No. 276,070, filed Nov. 25, 1988, now abandoned.

BACKGROUND OF THE INVENTION

The present invention pertains to the art of medical diagnostic imaging and more particularly to computerized tomographic (CT) scanners. The invention finds particular application in conjunction with cooling systems associated with CT scanners and will be described with particular reference thereto. It will be appreciated, however, that the invention has broader applications and may be advantageously employed in other environments.

CT scanner cooling systems of the type to which this invention pertains have ordinarily included air conditioning units housed within CT scanner gantries. Such air conditioning units were deemed necessary because they cooled sensitive radiation detectors and other components associated with the CT scanners. When a CT scanner is in operation, an X-ray beam rotates rapidly in a patient examination region. A rotating anode X-ray tube rotates continuously around the examination region and causes the beam to so rotate. The X-ray anode generates a significant amount of heat as well as the X-rays. Because the radiation detectors lost linearity and failed prematurely when heated, they were kept cool. Air conditioning units have been used to maintain radiation detectors at a proper working temperature. A typical CT scanner cooling system is illustrated in U.S. patent application Ser. No. 441,903, filed Nov. 15, 1982, now abandoned.

The use of air conditioning systems in connection with CT scanners has several drawbacks. First, the air conditioning units take up valuable space within the CT scanner gantry. The units are relatively cumbersome, and limit the amount of space available for the various CT scanner features.

Second, air conditioning units require frequent maintenance. If the air conditioning unit breaks down, the detectors can overheat during CT scanner use. Further, the air conditioning units are not readily removable. Their position within a CT scanners makes it difficult to repair other CT scanner parts and features by inhibiting free access to such parts.

The present invention contemplates a new and improved apparatus which overcomes all of the above-referenced problems and others.

SUMMARY OF THE INVENTION

In accordance with the present invention, a CT scanner is provided. A radiation source mounted to a rotating frame rotates a beam of radiation about an examination region. A plurality of radiation detectors receive radiation that has transversed the examination region from the source, and produce electrical signals indicative of the intensity of received radiation. An image reconstruction means reconstructs an image representation from the electrical signals. A cooling duct supplies cooling air to the heat sensitive radiation detectors.

In accordance with a more limited aspect of the present invention, the cooling duct is disposed about the periphery of the examination region. The duct is formed with a front panel of the CT scanner. The front panel includes an upper portion and a lower portion which are separately removable from a closed position on the CT scanner to an open position away from the scanner. The upper and lower panel portions are configured so that the cooling duct segments defined by the upper and lower panel portions sealingly abut when the upper and lower panel portions are in closed position. A pair of concentric flanges extend from the cooling duct to define a thin circular nozzle directed away from the panel and inward toward the radiation detectors. Pressurized ambient air enters the duct through air inlet means, and the air circulates throughout the duct and is forced through the circular nozzle to flow across the detectors. In this manner, the temperature of the detectors is regulated during CT scanner operation.

One advantage of the present invention is that air conditioning units are no longer required to cool heat sensitive radiation detectors. Accordingly, the costly and time consuming maintenance required for the air conditioning units is no longer necessary. Ambient air is freely and readily available for use in conjunction with the cooling duct of the present invention.

Another advantage of the present invention resides in the simplicity of the cooling duct. Because the cooling duct is integrally formed with the removable front panel, it can be easily removed and cleaned. There is little other maintenance required for the cooling duct. Further, because the entire duct work is easily removed, maintenance operations on the other parts of the CT scanner are facilitated. Finally, because the duct is a structural part of the front panel, it saves valuable space within the gantry.

Still other advantages and benefits of the present invention will become apparent to those skilled in the art upon reading and understanding the following detailed description of the preferred embodiment.

BRIEF DESCRIPTION OF THE DRAWINGS

The present invention may take form in various parts and arrangements of parts, and various steps and arrangements of steps. The drawings are only for purposes of illustrating preferred embodiments and are not to be construed as limiting the invention.

DETAILED DESCRIPTION OF THE PREFERRED EMBODIMENTS

Figure 1:
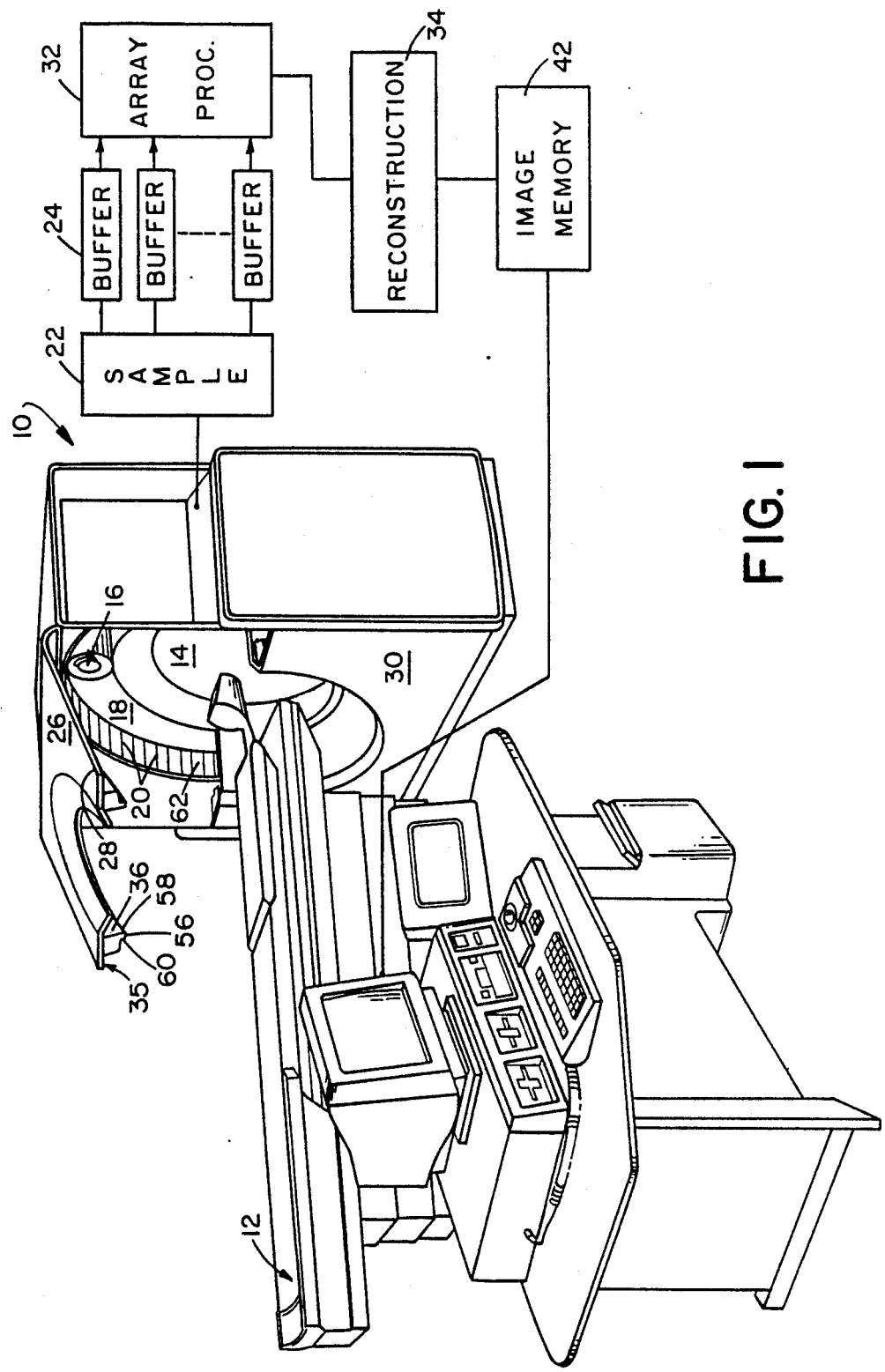
FIG. 1 is a diagrammatic illustration of a CT scanner in accordance with the present invention.

With reference to FIG. 1, a CT scanner 10 selectively images cross sectional slices of a region of a patient supported on a stationary patient couch 12 within a scan circle or examination region 14. In some applications, the patient couch is incremented to take a plurality of parallel slices. In another embodiment, the couch moves continuously such that the patient is scanned along helical paths. A rotating anode X-ray tube or radiation source means 16 for emitting a fan shaped beam of radiation toward and spanning the scan circle 14 is mounted to a rotatable gantry 18. Alternatively, a multispot X-ray tube may be utilized to increase the thickness of the fan beam or generate plural parallel beams. A plurality of thin radiation detectors 20 receive radiation which has transversed the examination region 14 from the X-ray tube 16.

With further reference to FIG. 1, electrical output signals indicative of the amount of radiation received by detectors 20 are sampled by sampling means 22. Preferably 1200 or more radiation detectors surround the examination region. Buffer memories 24 store the sampled data until a preprocessor means 32 digitizes the signals and performs digital signal processing operations, as are known in the art. Preprocessed detector data are reconstructed into an image representation by an image reconstruction means 34 such as a convolution and filtered back projection algorithm. The image representation may be stored in one or more image memories 42. The image memories may be selectively displayed on one or more video monitors. Alternately, the image representations may be stored in computer memory, stored on tape, subject to further processing, or the like.

Figure 2:
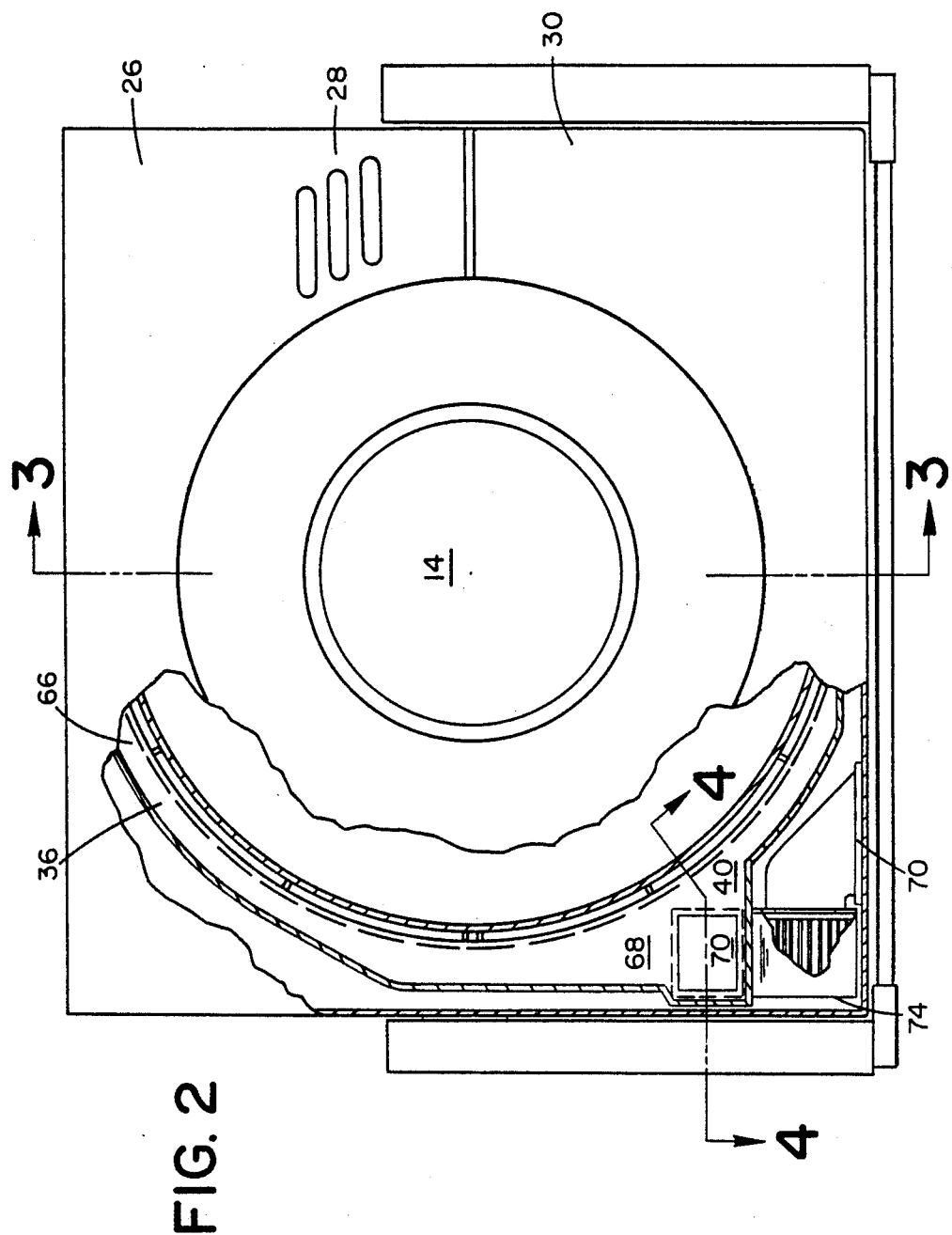
FIG. 2 is a front elevational view of a CT scanner with the cooling duct of the present invention shown in cut away.

With reference now to FIG. 2, a front panel, gantry cover or door 26 of a CT scanner is shown. The door 26 is generally planar on an exposed outer surface and slopes inward around the examination region. The door is comprised of at least two distinct and separately removable portions 28 and 30. Upper portion 28 can remain intact on the CT scanner 10 while bottom portion 30 is removed for cleaning, maintenance or other purposes. Conversely, bottom portion 30 can remain intact on the CT scanner while upper portion 28 is pivoted upward about a top hinge as shown in FIG. 1. Alternatively, both portions 28 and 30 can be removed.

Figure 3:
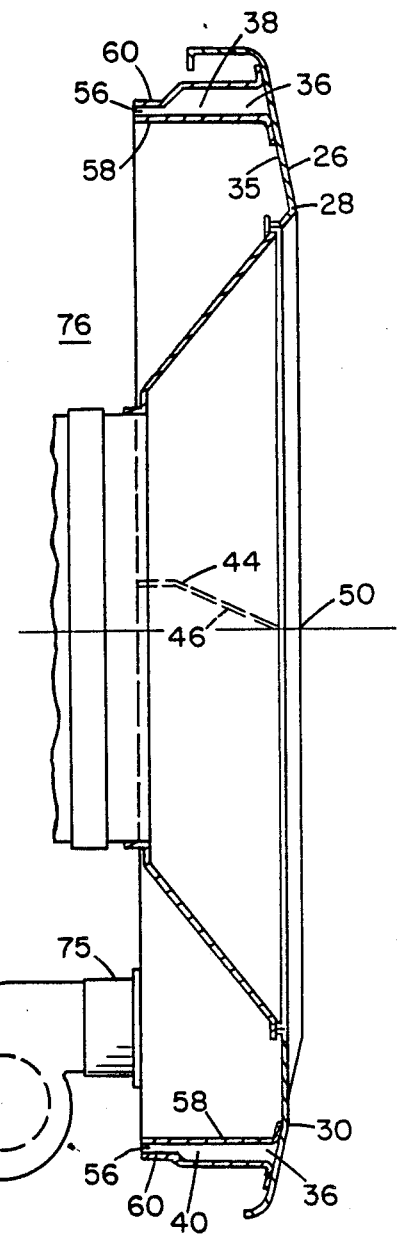
FIG. 3 is a cross sectional view taken along line 3—3 of FIG. 2.

A CT scanner cooling duct 36 is shown on FIG. 2. FIG. 3 shows that the cooling duct is structurally coupled with the door 26 on an inner door surface 35. The inner surface 35 of front door panel 26 provides at least one wall of the cooling duct 36. The duct is divided into a plurality of segments, particularly upper segment 38 and lower segment 40. When door bottom portion 30 is removed from the CT scanner, the lower cooling duct segment 40 is removed as well. Likewise, when upper door portion 28 is pivoted up, the upper cooling duct segment 38 is also moved.

With reference now to FIG. 3, and continuing reference to FIG. 2, it is apparent that the upper and lower door portions and the upper and lower cooling duct segments sealingly abut when the entire door panel 26 is in closed position. A bottom edge 44 of upper cooling duct segment 38 slopes generally inward and upward away from the front panel 26 toward the inner workings of the CT scanner. An upper edge 46 of the lower cooling duct segment 40 also slopes upward and inward from door panel 26. This enables the pivoted top panel duct to move freely into and out of abutment with the lower duct. The segment edges 44 and 46 are formed or machined to abut and form a tight seal when the door 26 is properly in closed position. The preferred embodiment does not call for the various cooling duct segments 38 and 40 to be fastened, clamped or otherwise adhered together or to compress a gasket. It is, though, to be understood that the upper and lower cooling duct segments could join together by other means. For instance, one of the segments could be telescopically received into the other. Alternately, the segments could snap together or compress a gasket. Still further, the cooling duct segments could be held together by a tongue and groove mating means. A seam 50 forms where upper and lower door portions 28 and 30 meet when the entire door panel 26 is in closed position.

Figure 4:
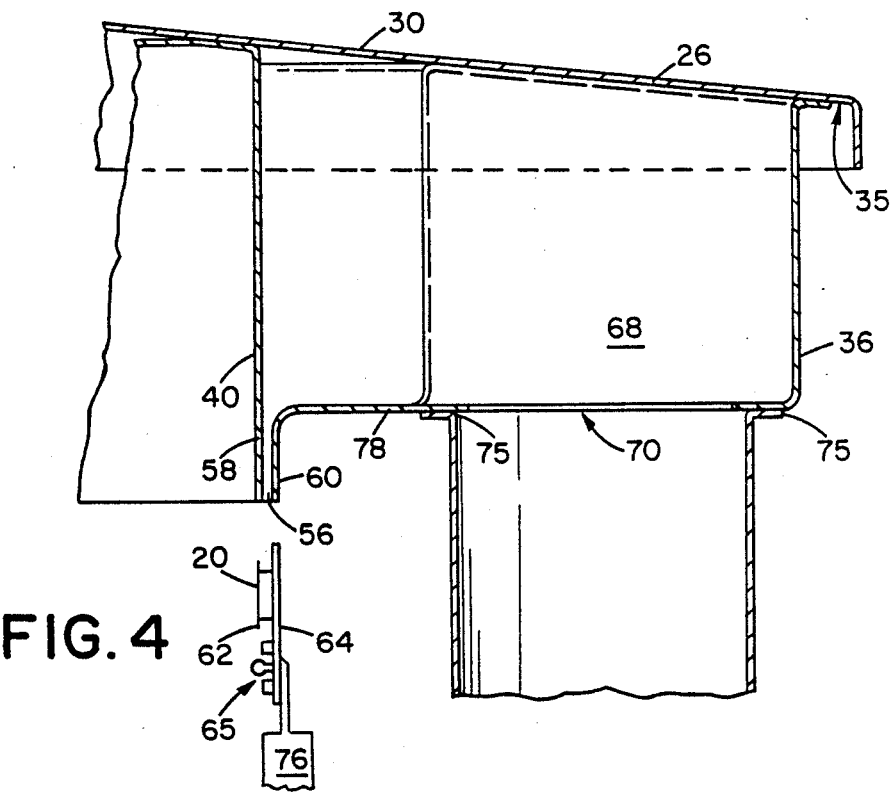
FIG. 4 is a cross sectional view taken along line 4—4 of FIG. 2.

As will be noted by FIGS. 2, 3 and 4, the cooling duct, as generally described by 36, surrounds the entire periphery of the examining region 14. The duct 36 also generally corresponds with the position of ring of detectors 20 about an inner wall of the CT scanner. The purpose of the cooling duct's shape and relative position is to provide a uniform flow of ambient air across all 1200 radiation detectors 20. The radiation detectors are heat sensitive, and when the X-ray tube 16 rotates around the examination region 14, the radiation detectors, as well as other instruments inside the CT scanner, tend to become overheated. When the detector temperature rises to a certain level, the detectors lose their ability to function properly. For this reason, the present invention provides a means by way of cooling duct 36 for cooling the detectors for maintaining them at a reasonable temperature or heat level.

Cooling duct 36 includes a circular but slit-like nozzle opening 56 defined by two concentric circular flanges 58 and 60. The nozzle opening 56, as disclosed in FIG. 4, directs ambient air which is present at elevated pressure in the cooling duct 36 generally away from the front door panel 26 and into the CT scanner 10. The air is primarily directed to pass through the nozzle 56 and over the detectors 20. Such a constant flow of air over the detectors maintains their temperature at a desirable level. It is to be noted that nozzle opening 56 is approximately of equal size to a thickness 62 of radiation detectors 20. The air ejected from the nozzle passes parallel to a circuit board 64 on which detectors or detector modules 20 and associated preamplifiers and other circuitry 65 are mounted.

Figure 6:
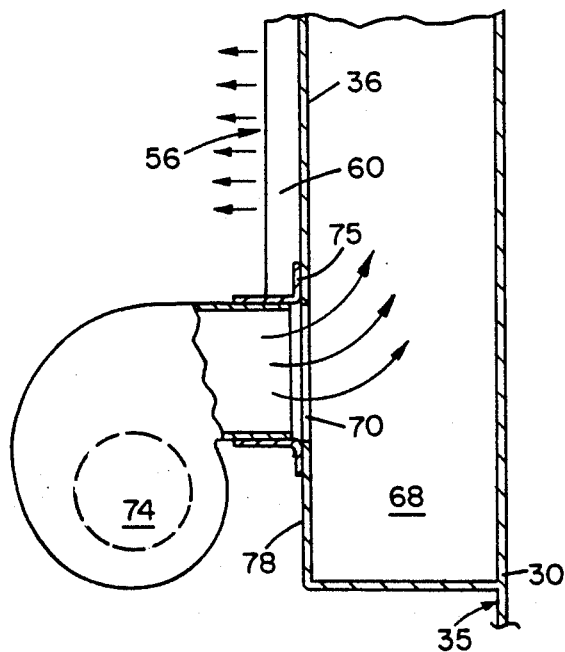

With reference again to FIGS. 2 and 3, and further reference to FIG. 6, the cooling duct 36 defines a cavity 66 which completely encircles the examination region 14. The cavity is somewhat larger at areas designated 68. At least two air inlet means 70 are associated with these larger cavity areas 68. These air inlet means allow air to enter the duct through lower duct segment 40. Once air enters the lower duct segment it readily circulates through the upper segment 38 as well. Room air is filtered before it enters the cooling duct.

A pump, fan or other pressurizing means 74 for supplying ambient air to the cooling duct 36 is associated with air inlet means 70. The fan 74 has an outlet flange 75 that frictionally abuts an inner surface of the enlarged duct area 68 surrounding apertures 70. A similar fan and inlet assembly is disposed on the other side of the duct. Pressurizing means 74 assures that the air within cooling duct 36 is at a pressure elevated beyond standard air pressure. The pressure differential between the cooling duct 36 and an inner region 76 of the CT scanner 10 is such that air continuously flows through nozzle opening 56 and across radiation detectors 20. Such air flow keeps the detectors 20 cool.

With particular reference to FIG. 4, a cross sectional view along line 4—4 of FIG. 2 is shown. As can be seen, air inlet means 70 provide no obstruction in enlarged area 68 of cavity 66. FIG. 4 further provides another view of cooling duct 36 with nozzle opening 56 directed inward toward the scanner inner region 74 and away from door panel 26. The nozzle 56 is directed to pass air across detector 20.

Figure 5:
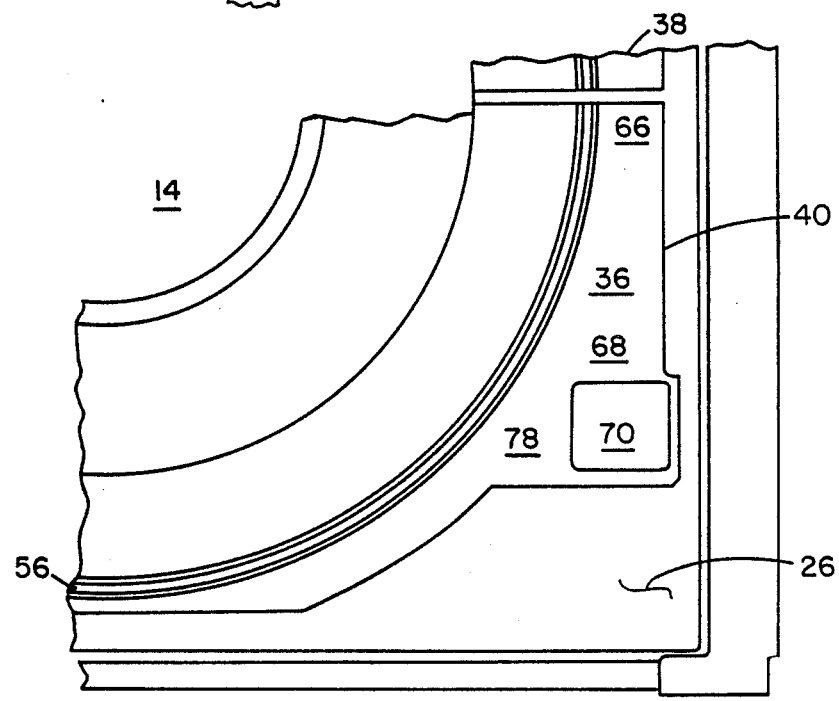
FIG. 5 is a segment of a view of an interior side of a front panel of the present invention showing a portion of the cooling duct thereon; and, FIG. 6 is a partial cross sectional view of the cooling duct and diagrams air flow therethrough.

FIG. 5 shows an elevational view of a section of the bottom portion 30 of door panel 26 and cooling duct 36. The section is removed from the scanner but is the portion of the panel that faces the interior region 76. As will be noted, air inlet means 70 are openings defined by an inner wall 78 of cooling duct 36. Inner wall 78 is displaced from and parallel to front door panel 26.

The invention has been described with reference to the preferred embodiment. Obviously, modifications and alterations will occur to others upon reading and understanding the preceding detailed description. It is intended that the invention be construed as including all such alterations and modifications insofar as they come within the scope of the appended claims or the equivalents thereof.

Having thus described the preferred embodiment, the invention is now claimed to be:

1. A CT scanner comprising:
   a means for describing an examination region;
   a radiation source means for rotating a beam of radiation about the examination region;
   a plurality of radiation detectors for receiving radiation which has transversed the examination region from the source means and for producing electrical signals indicative of the received radiation;
   image reconstruction means for reconstructing the electrical signals into an image representation;
   a panel defining a wall for shielding the source means and radiation detectors from exposure to surrounding elements; and,
   a cooling duct peripherally disposed about the examination region and at leas&: partially defined by the panel.

2. The CT scanner of claim 1 wherein the panel is detachably received on the CT scanner.

3. The CT scanner of claim 2 wherein the panel includes an upper portion and a lower portion, each panel portion separately removable from a closed position on the CT scanner to an open position away from the scanner, and together defining a single outer surface plane when in closed position, each panel portion further defining on an inner surface a segment of the cooling duct.

4. The CT scanner of claim 3 wherein the panel upper and lower portion cooling duct segments sealingly abut when the upper and lower panel portions are in closed position.

5. The CT scanner of claim 1 wherein circular concentric flanges project from the cooling duct, generally inwardly into the scanner and generally away from the panel.

6. The CT scanner of claim 5 wherein the concentric flanges define a nozzle directed away from the panel and inward toward the radiation detectors.

7. The CT scanner of claim 6 wherein the cooling duct includes at least one air inlet means.

8. The CT scanner of claim 7 wherein a pressure means associated with the air inlet means forces ambient air to flow within the cooling duct at an elevated pressure, the pressurized air in the duct further forced out through the nozzle and over the detectors for regulating the temperature of the detectors.

9. The CT scanner of claim 1 wherein at least one-half of the cooling duct is disposed on the removable panel.

10. The CT scanner of claim 9 wherein the cooling duct is completely disposed on the removable panel.

11. The CT scanner of claim 1 wherein the cooling duct provides a substantially unobstructed passageway for ambient air to circulate around the examination region and across the radiation detectors for cooling the detectors during scanner operation.

12. A radiographic apparatus comprising:
    a means for describing an examination region;
    a radiation source means for rotating a beam of radiation about the examination region;
    a ring of radiation detectors for receiving radiation which has transversed the examination region from the source means and for producing electrical signals indicative of the received radiation;
    image reconstruction means for reconstructing the electrical signals into an image representation;
    a cooling duct for conveying air to a nozzle disposed peripherally about the examination region contiguous to the ring of detectors, said cooling duct at least partially defined by a removable door panel.

13. The radiographic apparatus of claim 12 wherein the cooling duct includes a plurality of walls which define a cavity that extends around the examination region.

14. A radiographic apparatus comprising:
    a means for defining an examination region;
    a radiation source means for rotating a beam of radiation about the examination region;
    a ring of radiation detectors for receiving radiation which has transversed the examination region from the source means and for producing electrical signals indicative of the received radiation;
    an image reconstruction means for reconstructing the electrical signals into an image representation;
    a cooling duct for conveying air to a nozzle disposed peripherally about the examination region contiguous to the ring of detectors, the cooling duct including a plurality of walls which define a cavity that extends around the examination region; and,
    a nozzle defined by circular concentric flanges which project from the cooling duct generally inward toward the radiation detectors.

15. The radiographic apparatus of claim 14 wherein the nozzle directs air parallel to a face of the radiation detectors.

16. The radiographic apparatus of claim 15 wherein the cooling duct includes at least one air inlet means.

17. The radiographic apparatus of claim 16 wherein a pressure means associated with the air inlet means forces ambient air to flow within the cooling duct at an elevated pressure, the pressurized air in the duct further forced out through the nozzle and over the detectors for regulating the temperature of the detectors during CT scanner operation.

18. A radiographic apparatus comprising:
    a means for defining an examination region;
    a radiation source means for rotating a beam of radiation about the examination region;
    a ring of radiation detectors for receiving radiation which has transversed the examination region from the source means and for producing electrical signals indicative of the received radiation;
    an image reconstruction means for reconstructing the electrical signals into an image representation;
    a cooling duct for conveying air to a nozzle disposed peripherally about the examination region contiguous to the ring of detectors, the cooling duct being mounted on a removable door panel.

19. A CT scanner comprising:
    a means for defining an examination region;

a radiation source means for rotating a beam of radiation about the examination region;

a plurality of radiation detectors for receiving radiation which has transversed the examination region from the source means and for producing electrical signals indicative of the received radiation;

an image reconstruction means for reconstructing the electrical signals into an image representation;

a panel defining a wall for shielding the source means and radiation detectors from exposure to surrounding elements; and, a cooling duct for conveying air to a generally circular outlet peripherally disposed about the examination region, the outlet defined by circular concentric flanges which project inward from the cooling duct to direct air over the radiation detectors for regulating the temperature of the detectors during CT scanner operation.

20. A radiographic apparatus comprising:

a means for describing an examination region;

a radiation source means for rotating a beam of radiation about the examination region;

a plurality of radiation detectors disposed along a circular ring of a ring diameter for receiving radiation which has transversed the examination region from the source means and for producing electrical signals indicative of the received radiation;

image reconstruction means for reconstructing the electrical signals into an image representation;

a panel defining a wall for shielding the source means and radiation detectors from exposure to surrounding elements; and, a cooling duct for conveying air to an outlet peripherally disposed about the examination region, the outlet defined by circular concentric flanges of generally the ring diameter which project inward from the cooling duct to direct air over the radiation detectors for regulating the temperature of the detectors during CT scanner operation.

* * * * *